(12) United States Patent
Wood et al.

(10) Patent No.: US 8,603,000 B2
(45) Date of Patent: Dec. 10, 2013

(54) METHOD AND APPARATUS FOR MEASURING BLOOD VOLUME

(75) Inventors: Kim Wood, London (CA); P. Chad Hodgson, Salford (CA); Peter Plouf, London (CA)

(73) Assignee: Transonic Scisense Inc., London (CA)

( * ) Notice: Subject to any disclaimer, the term of this patent is extended or adjusted under 35 U.S.C. 154(b) by 0 days.

(21) Appl. No.: 13/465,796

(22) Filed: May 7, 2012

(65) Prior Publication Data

US 2012/0220886 A1    Aug. 30, 2012

Related U.S. Application Data

(62) Division of application No. 12/108,434, filed on Apr. 23, 2008, now abandoned.

(60) Provisional application No. 60/913,734, filed on Apr. 24, 2007.

(51) Int. Cl.
*A61B 5/02* (2006.01)
*A61B 5/06* (2006.01)

(52) U.S. Cl.
USPC ........... 600/507; 600/508; 600/486; 600/481; 600/547

(58) Field of Classification Search
None
See application file for complete search history.

(56) References Cited

U.S. PATENT DOCUMENTS

| | | |
|---|---|---|
| 3,730,171 A | 5/1973 | Namon |
| 4,380,237 A | 4/1983 | Newbower |
| 4,674,518 A | 6/1987 | Salo |
| 4,796,641 A | 1/1989 | Mills et al. |
| 4,846,191 A | 7/1989 | Brockway et al. |
| 4,899,759 A | 2/1990 | Pederson et al. |
| 4,945,762 A | 8/1990 | Adamic, Jr. |
| 5,058,582 A | 10/1991 | Thaler |
| 5,058,583 A | 10/1991 | Geddes et al. |
| 6,033,366 A | 3/2000 | Brockway et al. |
| 6,409,674 B1 | 6/2002 | Brockway et al. |
| 6,454,710 B1 | 9/2002 | Clift |
| 6,494,832 B1 | 12/2002 | Feldmann et al. |
| 6,718,190 B2 | 4/2004 | Krivitski et al. |
| 7,483,743 B2 | 1/2009 | Mann et al. |
| 7,803,121 B2 | 9/2010 | Plouf et al. |
| 8,090,432 B2 | 1/2012 | Cinbis et al. |
| 8,126,534 B2 * | 2/2012 | Maschke ................ 600/424 |
| 8,460,198 B2 * | 6/2013 | Plouf et al. ............. 600/486 |
| 2003/0130570 A1 | 7/2003 | Krivitski et al. |
| 2004/0147969 A1 | 7/2004 | Mann et al. |
| 2007/0043298 A1 | 2/2007 | Plouf et al. |
| 2008/0269581 A1 | 10/2008 | Wood et al. |
| 2011/0098584 A1 | 4/2011 | Plouf et al. |

FOREIGN PATENT DOCUMENTS

WO    WO 2005/121780 A2    12/2005

* cited by examiner

*Primary Examiner* — Nita M Minnifield
(74) *Attorney, Agent, or Firm* — John R. S. Orange; Blake, Cassels & Graydon LLP

(57) ABSTRACT

In one aspect, a conductance catheter is provided for measuring the volume of a fluid. The conductance catheter comprises a series of electrodes and a circuit to compensate for variations in sensitivity of the electrodes in the catheter. In another aspect, a resistivity sensor is provided for determining the resistivity of a fluid. The sensor comprises a series of electrodes spaced such that the total distance between endmost electrodes does not exceed the diameter of the catheter deploying the sensor.

10 Claims, 16 Drawing Sheets

METHOD AND APPARATUS FOR MEASURING BLOOD VOLUME

This application is a divisional of U.S. patent application Ser. No. 12/108,434 filed on Apr. 23, 2008, which claims priority from U.S. Provisional Application No. 60/913,734 filed on Apr. 24, 2007, the contents of both applications being incorporated herein by reference.

TECHNICAL FIELD

The present invention relates generally to data acquisition systems and particularly to measuring blood volume in a living organism.

DESCRIPTION OF THE PRIOR ART

In the field of cardiac research the standard test for measuring cardiac efficiency is the pressure volume graph. This test correlates Left Ventricle (LV) chamber pressure and volume as the heart contracts and expands. Pressure and volume values are important for quantifying efficiency in any pump system, and can be used to calculate volumetric efficiency of such systems. Cardiac efficiency is a useful measurement for studying heart disease, by quantifying the progress of the disease and measuring the effectiveness of the treatment.

Recently, gene altered mice have increased in popularity as a means for studying heart disease, and for modelling human heart disease. Typically, LV data is measured using a catheter that is inserted into the LV. The catheter typically has separate instrumentation for measuring blood pressure and blood volume. There are several drawbacks to using data taken from anaesthetized mice, most significantly the fact that it has been found that cardiovascular data taken from an anaesthetized specimen differs significantly from free-roaming specimens.

In order to measure cardiovascular data from a free-roaming specimen, an implanted device is required that can operate while the specimen is active, and transmit data to the exterior of the specimen for processing. This need presents several design problems, notably size and battery life. Particularly, a reduced size provides a less invasive device, and a longer battery life decreases the number of surgical operations required to change or recharge a device. The need to reduce repeated trauma due to surgery and the cost of the surgery are driving reasons for the need to extend battery life in biological implants. These concerns are heightened when extending the application to human specimens.

There are numerous devices that have been developed for measuring physiological pressure in living specimens, e.g., those shown in U.S. Pat. Nos. 4,796,641; 4,846,191; and 6,033,366. These devices include a catheter having a pressure sensor that is inserted into an area in the specimen having a physiological pressure, such as an artery. The sensors include a pressure transmitting catheter filled with a pressure transmitting fluid. A pressure transducer communicates with the fluid to provide an electric pressure signal representing variations in physiological pressure that can be transmitted to the exterior of the specimen. These devices are only concerned with measuring pressure, and the use of a fluid filled catheter can lead to undesirable frequency response characteristics and may exhibit head pressure artefacts.

Other devices, e.g., that shown in U.S. Pat. No. 6,409,674 provide an implantable sensor being anchored to the interior wall of the LV in a living specimen. The sensor acquires and transmits data from within the heart to an external data receiver. This device is concerned with only measuring a single parameter, and specifically illustrates measuring pressure.

The volume of a liquid in a cylindrical chamber, such as the left ventricle of a heart, can be derived by measuring the conductance of the fluid. The volume (V) can be calculated according to the following equation:

$$V = \frac{1}{\alpha}\rho L^2 G.$$

The variable α represents a non dimensional correction factor attribute to the fact that the electrical field created with catheter based volumetry is not typically uniform in its distribution throughout the blood volume. The variable ρ represents the resistivity of the blood in the LV. It is important for this value to be as accurate as possible and as representative of the actual blood inside the volume being measured. This variable has the potential to change over time or due to research intervention and thus cannot be considered always consistent. The resistivity has been shown to vary with temperature, hematocrit and blood velocity. Moreover, it is possible that changes in electrolyte concentrations also alter resistivity. The variable L represents the distance between the sensing electrodes, which is fixed by the nature of the catheter or other measurement instrument being used. Finally, G is the actual conductance value that is measured by the electrodes. G may include a correction factor for an overestimation of G caused by the electric field entering the muscle. Such a correction may then represent G as $G=G_{blood}-G_{correction}$.

Both α and ρ can be problematic to measure when performing conductance based cardiac volumetry, since while conductance based cardiac volume is a widely used, its accuracy is limited by the non-uniformity of the transmitted electric field and the non-fixed value of the blood resistivity.

Studies have shown that the positioning of a catheter or other measuring device in, e.g., a ventricular chamber, is important in accurately determining volume. In particular, this can occur when the catheter is not centred within the chamber. However, knowing the position of the catheter within the ventricle can be difficult with existing technology and relies upon the user's objective skill and experience.

It is therefore an object of the following to obviate or mitigate at least one of the above-mentioned disadvantages.

SUMMARY OF THE INVENTION

In one aspect, there is provided a sensing tip for measuring the volume of a fluid comprising one or more electrodes for measuring the volume and a resistivity sensor disposed on the tip in communication with the fluid to incorporate a current measurement of resistivity during measurement of the volume.

In another aspect, there is provided a system for measuring volume of a fluid comprising a sensing tip having a plurality of pairs of electrodes, each pair of electrodes being connected to a circuit to compensate for variations in sensitivity of respective pairs of electrodes according to the positioning of the respective pairs along the sensing tip.

In yet another aspect, there is provided a method for calibrating a sensing tip used for measuring volume of a fluid comprising inserting the sensing tip into a plurality of cuvettes containing fluids having differing properties, and when in each well, the method comprises: obtaining a plurality of conductance signals using a plurality of electrodes on the sensing tip; adjusting the conductance signals to compensate for variations is sensitivity of the pairs of electrodes due to the positioning of the electrodes along the sensing tip; obtaining a measurement of resistivity; and using the conductance signals and the measurement of resistivity to calibrate the sensing tip.

In yet another aspect, there is provided a method for positioning a sensing tip disposed in a ventricle comprising obtaining an excitation waveform generated by one pair of electrodes disposed on the sensing tip; obtaining a conductance waveform sensed by another pair of electrodes disposed on the sensing tip; comparing the waveforms to determine a phase shift between the waveforms; and adjusting the positioning until the phase shift is deemed acceptable.

BRIEF DESCRIPTION OF THE DRAWINGS

An embodiment of the invention will now be described by way of example only with reference to the appended drawings wherein.

DETAILED DESCRIPTION OF THE DRAWINGS

A system and method are provided for accurately handling the parameters for measuring blood volume in real time. In particular, it has been found that in order to perform accurate and repeatable conductance measurements (parameter G), it is important to eliminate variations in the measuring electrode sensitivity from the equation. The following provides a calibration circuit that takes into account electrode sensitivity at the time of calibration and thus eliminates such variability. This also compensates for the non-uniformity of the electric field generated by a conductance measuring device. In order to compensate for the electrode sensitivity, an adjustable gain and offset can thus be used in each segment of a conductance measurement.

In the following, a resistivity sensor is also provided such that the resistivity (parameter $\rho$) is measured on a continuous or as-needed basis rather than at time-spaced intervals or relying on a "most recent" measurement. This compensates for variations in resistivity discussed above and thus provides more accurate volume measurements.

The calibration and resistivity sensor can be incorporated into any deployable medical device such as an implant or catheter. The following example describes an implant transmitter, however, it will be appreciated that the principles for measuring resistivity and for calibrating volume measurements discussed herein are equally applicable to other devices such as catheters.

It will also be appreciated that the following principles are also applicable to measuring volume in any fluid and should not be considered limited only to blood.

Also provided is a system and method for determining the position of a catheter or other measuring device in a ventricle by comparing excitation and sensed waveforms and correcting the position until the phase angle is minimized.

Figure 1:
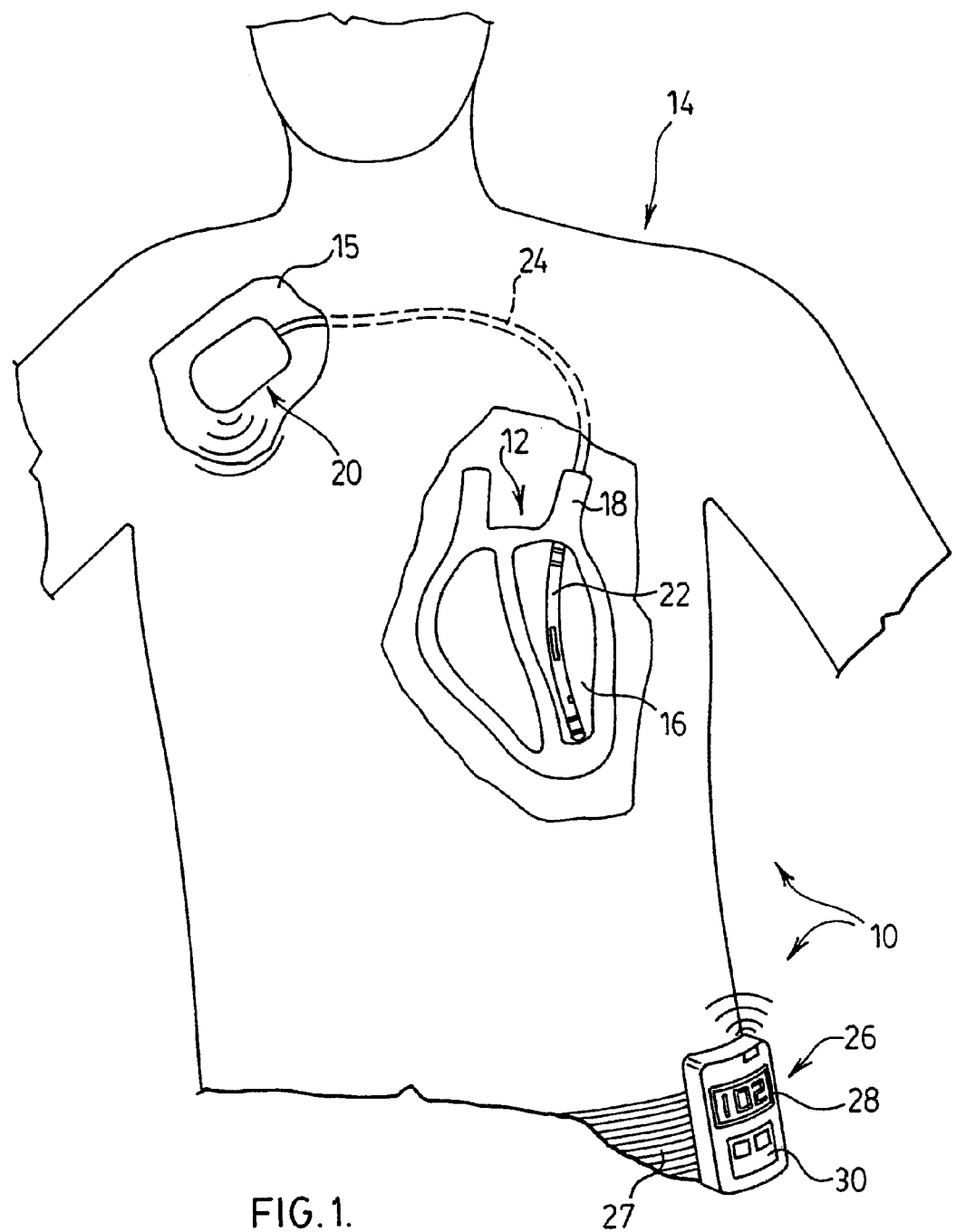
FIG. 1 pictorially shows a wireless cardiovascular data acquisition system.

Referring now to FIG. 1, one embodiment of a wireless cardiovascular data acquisition system is generally denoted by numeral 10. The system 10 operates to measure physical parameters of a heart 12 located within a body 14. The heart 12 and body 14 form part of a living organism, such as a gene altered mouse or a human. The heart 12 includes a heart chamber, in this example a Left Ventricle (LV) 16 that in part communicates with the body 14 via a heart valve 18. A sensing tip 22 is situated in the LV 16 by insertion thereof through the valve 18, and has a communication path 24 leading to a transmitting device 20 implanted in a portion 15 of the body 14, which in this example is external to the heart 12. In the example shown in FIG. 1, the portion 15 is in proximity of the body's clavicle. It will be appreciated that the transmitting device 20 may be situated anywhere as desired, e.g. within the heart 12 or heart chamber (i.e. LV 16).

The transmitting device 20 wirelessly transmits data to a receiving device 26 that in this example is attached to a belt 27 external to the body 14. The receiving device 26 may display data on a screen 28 as shown in FIG. 1, and may comprise a keypad 30 for scrolling between different views. A schematic of the system 10 is shown in FIG. 2.

Figure 2:
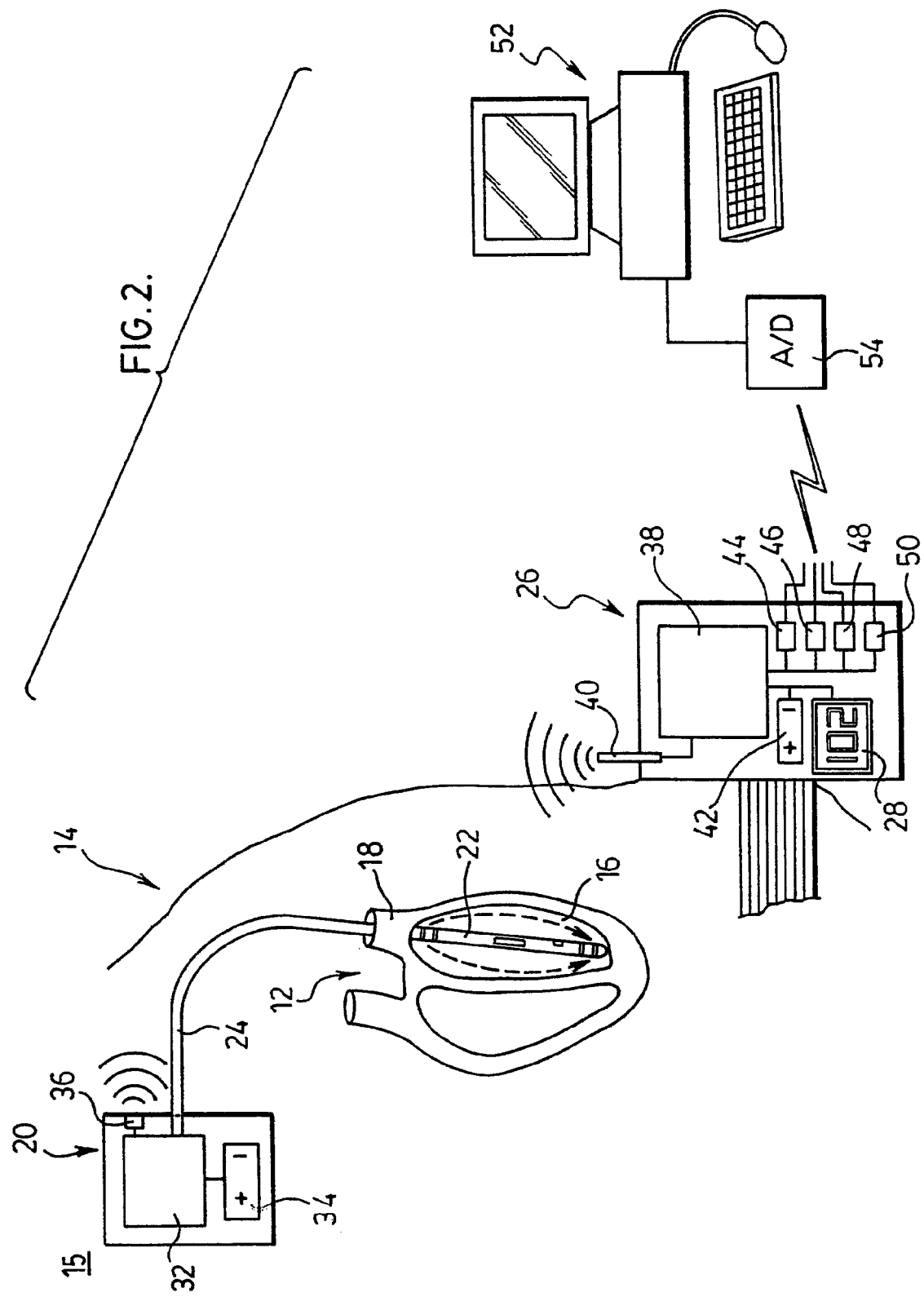
FIG. 2 is a schematic representation of the system of FIG. 1.

Referring now to FIG. 2, the path 24 communicates data acquired by the sensing tip 22 to a transmitter processing module 32 in the transmitting device 20. The transmitting device 20 is powered by obtaining energy from a battery 34, and has a transmitter 36. It will be appreciated that the use of a battery 34 is for illustrative purposes only and that any suitable means for powering the transmitting device 20 may be used such as power scavenging (converting environmental energy into electricity) or RF power transmission (energy transmitted to the device 20 from an external source through a radio frequency signal).

Since the processing module 32 is preferably implanted in the body 14, the signal sent via the transmitter 36 should pass through body tissue before reaching the air. The attenuation of an RF signal by different body materials is typically highly frequency dependent. Therefore, the transmitter 36 should be selected so as to minimize the attenuation of the signal it transmits. Typically, a lower frequency is preferred to transmit the signals since the lower the frequency, the greater the depth of penetration. However, the lower the frequency, the higher the wavelength and thus the longer the antenna required at the receiving end. Therefore, the transmitter 36 should be chosen to balance these requirements depending on the particular application. A suitable frequency to achieve such a balance is 40 MHz. The power consumed by the transmitter 36 should also be considered so that it can be faithfully detected at its receiving end whilst conserving energy.

The transmitting device 20 communicates wirelessly with the receiving device 26 through a receiver 40. The device 26 has a receiver processing module 38 that is adapted for processing data received from the device 20. The device 26 is powered by a battery 42 or suitable AC or DC power source (not shown). The device 26 has a series of signals (44-50) for providing electrical representations of measurements acquired using the sensing tip 22, including a pressure signal 44, a volume signal 46, a temperature signal 48, and an electrocardiogram (ECG) signal 50.

In FIG. 2 these signals are shown as being external to the processing module 38 and communicably connected to an external computing device 52 having an analog-to-digital (A/D) converter 54 connected thereto. However, it will be appreciated that the A/D converter 54 may be included in either the processing module 38 or processing module 32, and computing device 52 may be replaced by any suitable alternative such as processing capabilities provided by the processing module 38. The communicable link between the receiving device 26 and the computing device 52 and/or A/D converter 54 may be any hardwired or wireless communication channel, e.g., using Bluetooth technology.

The computing device 52, external or internal to the receiving device 26, may be any device that is capable of acquiring data and communicating with the processing module 38. In the example shown in FIG. 2, the device 52 is a standard personal computer (PC) having a monitor, central processing unit (CPU), keyboard, and mouse.

Figure 3:
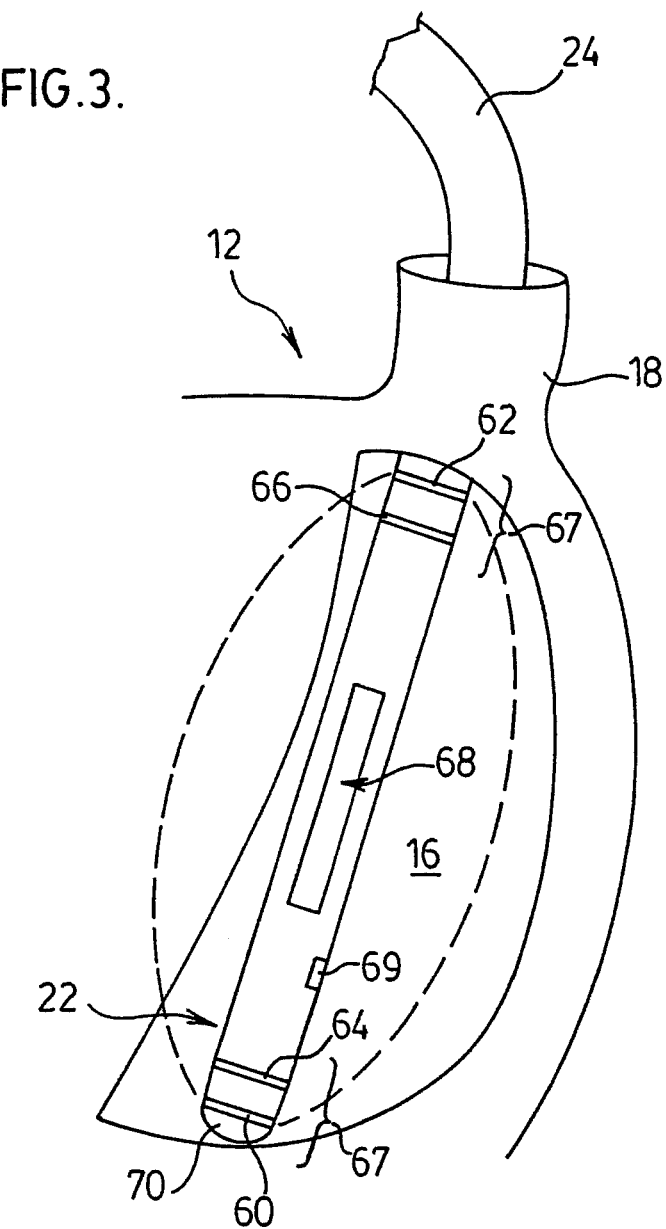
FIG. 3 is a magnified view of a portion the heart shown in FIG. 1.

The sensing tip 22 is shown in greater detail in FIG. 3. The sensing tip 22 has a rounded end 70 to facilitate the deployment thereof through the valve 18. In this example, a proximal electrode 62 and a distal electrode 60 each following the circumference of the sensing tip 22 flank a pair of inner electrodes 64, 66, a pressure sensing device 68, and a temperature sensing device 69. The electrodes 60, 62, 64 and 66 are used to measure the volume of blood in the LV 16 and are herein collectively referred to as the volume sensing device denoted by numeral 67. The proximal electrode 62 transmits a signal, and the distal electrode receives same to create an electric field in the LV 16. The inner electrodes 64, 66 sense this electric field to perform a conductance measurement indicative of the volume in the LV 16. The inner electrodes 64, 66 can be modeled conceptually as measurement probes on either side of a "resistor", wherein the "resistor" represents the resistivity of the blood in the LV 16, the inner electrodes 64, 66 are arranged to measure the potential across the "resistor". The volume measurement and/or volume signal may also be referred to as a conductance measurement and/or conductance signal respectively, and it will be appreciated that this terminology may herein be considered interchangeable.

The pressure sensing device 68 is used to sense the pressure of the blood in the LV 16. The temperature sensing device 69 is used to sense the temperature of the body 14, since it is substantially uniform throughout. The temperature sensing device 69 is preferably comprised of a thermistor or equivalent component. The volume sensing device 67, pressure sensing device 68, and temperature sensing device 69 communicate data to the transmitting device 20 through the path 24, thus the path 24 typically carries a number of wires, enabling data to be transmitted from the sensing tip 22 to the device 20. The length of the path 24 is dependent upon the location of the device 20 relative to the heart 12.

Although the temperature sensing device 69 is shown in FIG. 3 as part of the sensing tip 22, it will be appreciated that the device 69 may be situated anywhere in the body 14 enabling the internal temperature of the body 14 to be measured, and this may be inside or outside of the heart 12.

Figure 4A:
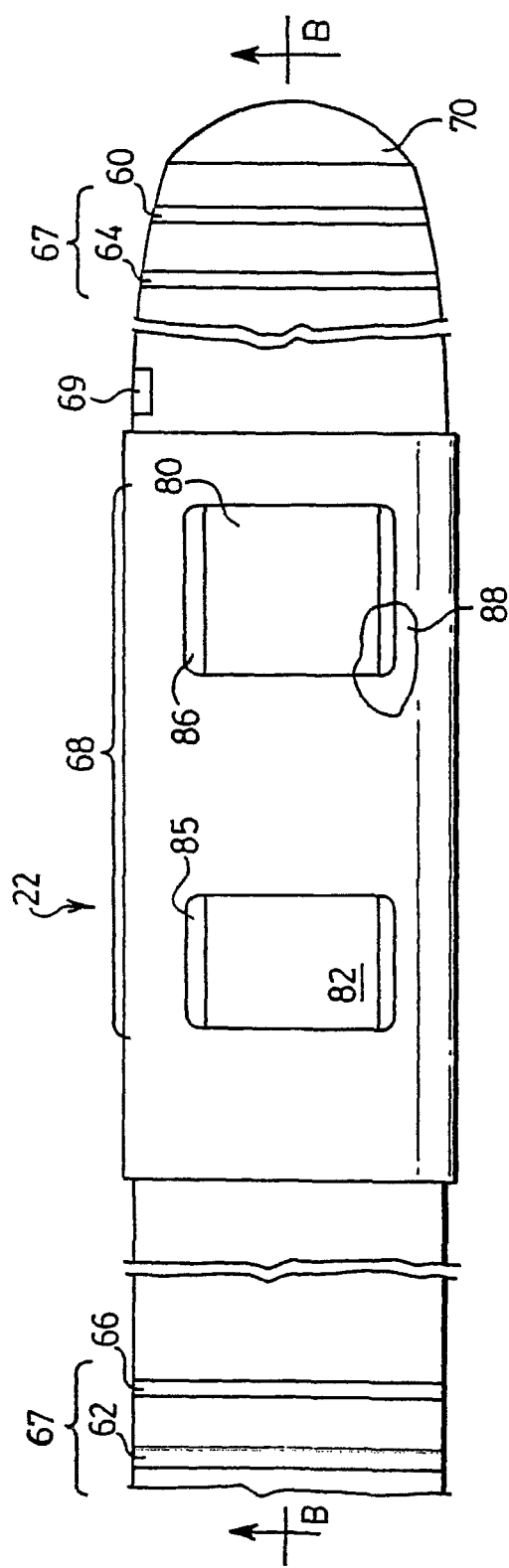
FIG. 4a is a partial plan view of the pressure sensing device of FIG. 2.
Figure 4B:
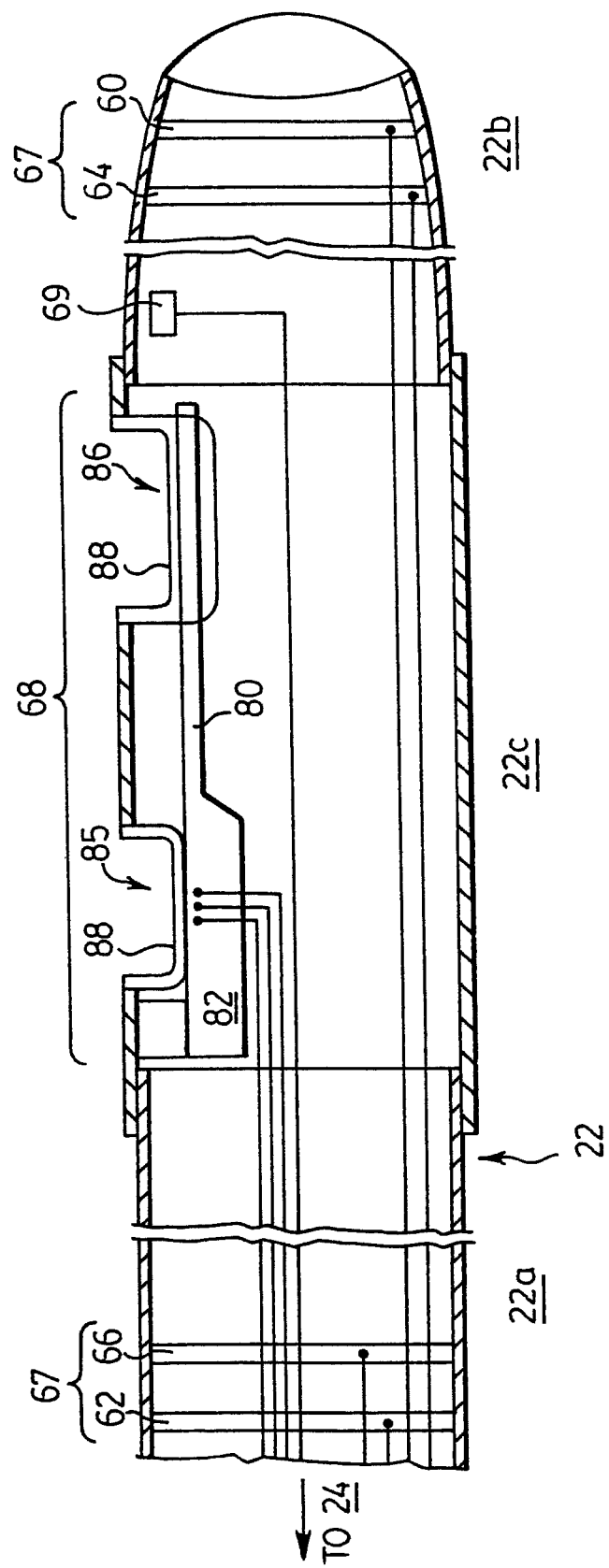
FIG. 4b is a sectional view of the sensing device shown in FIG. 4a along the line B-B.

An embodiment of the sensing tip 22 is shown in FIGS. 4a and 4b. It will be appreciated that the relative dimensions of the sensing tip 22 have been exaggerated for illustrative purposes only. The pressure sensing device 68 may be any device capable of sensing a pressure. In this example, the pressure sensing device comprises a piezoresistive deflection sensor, specifically a cantilevered sensor beam 80 having a base portion 82 that is attached to the housing of the sensing tip 22. A base window 85 in the sensing tip 22 enables the base of the beam 80 to experience external pressure, and a tip window 86 enables the tip of the beam 80 to experience external pressure. A layer of sealant 88 inhibits the beam 80 from direct contact with its surrounding environment. However, the layer 88 permits external pressure to effect flexure of the beam 80 due to variations in the pressure of the surrounding blood. It can be seen in FIG. 4b that electrical wires run from the sensing devices 67, 68 and 69 to the path 24.

Figure 5:
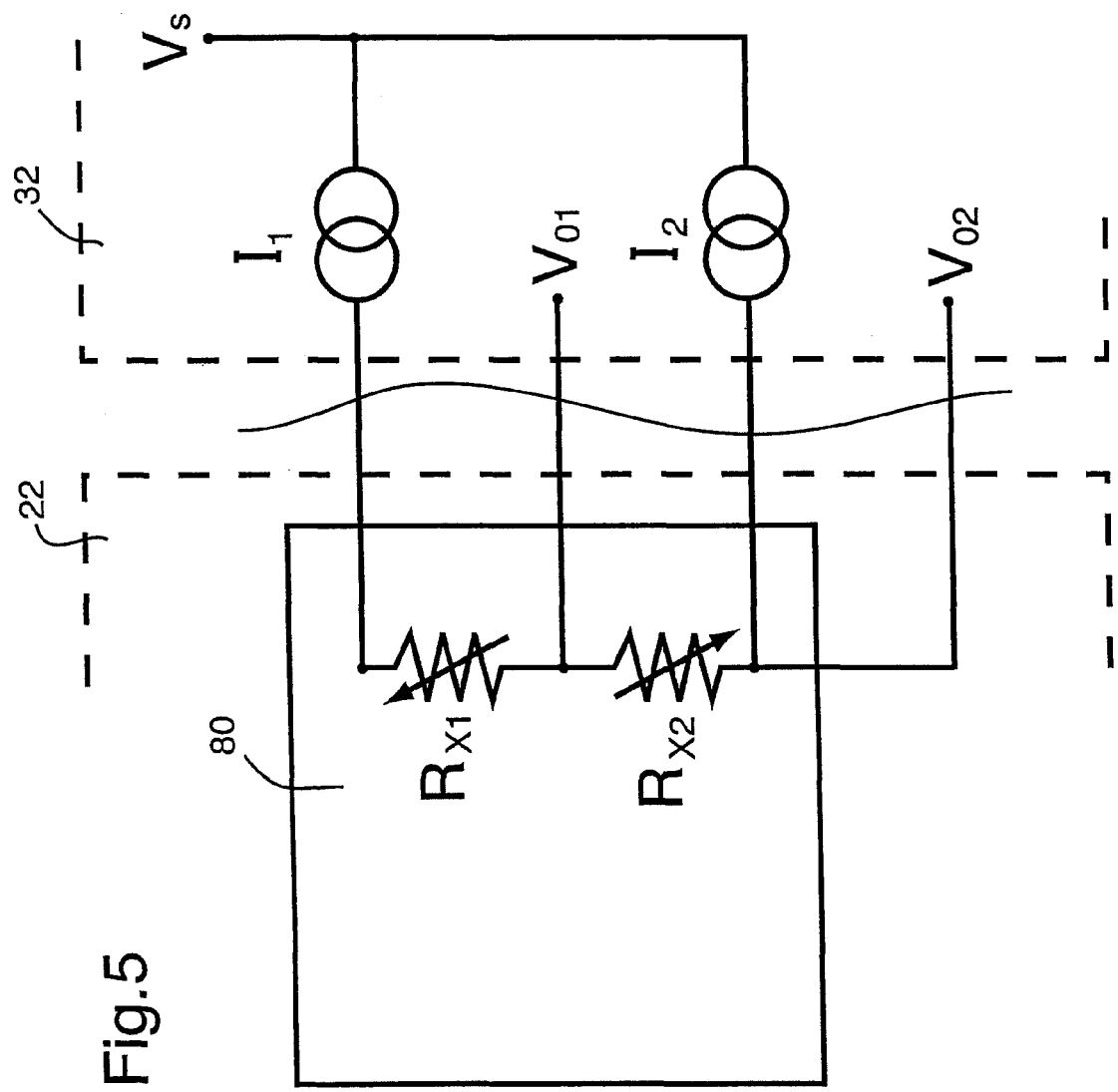
FIG. 5 is an electric schematic of the pressure sensing device.

An implementation of the beam 80 is shown schematically in FIG. 5, being a strain gauge sensor, on which two resistors $R_{x1}$ and $R_{x2}$ are mounted. When the beam bends as a result of a pressure experienced thereby, the resistances of these resistors change in opposite directions. That is, the resistance of one of the resistors increases while that of the other one decreases. As a result, the accompanying electronic circuits may be designed in a fully differential architecture which provides a higher signal to noise ratio (SNR) compared to a single ended architecture.

The following lists suitable specifications for the pressure sensing device 68, but shall in no way be considered limited thereto: nominal resistance of each resistor $R_{x1}$, $R_{x2}$ being 10,000 Ohms; gauge factor of 70-80; total resistor manufacturing tolerance of +/−10-15%; maximum resistance value mismatch between the resistors of 2.4%; temperature coefficient of resistance of +5%/100° F.; and a breakdown voltage of 20V.

These exemplary specifications illustrate that typically there may be non-idealities for the sensing device 68 that would preferably be addressed when designing the circuitry therefor. For instance, due to process variations, the resistances of $R_{x1}$ and $R_{x2}$ are in all likelihood not going to be equal. This may generate some offset at the output. Moreover, since the resistance of the resistors $R_{x1}$ and $R_{x2}$ is a temperature dependent parameter, the temperature coefficient of resistance (TCR) may cause an offset due to mismatch. Hence, even if the offset is cancelled at one temperature it may not be zero at another temperature. Finally, the temperature coefficient of the gauge factor (TCGF) makes the gain of the sensing device 68, temperature dependent.

The above parameters are typically sources for measurement inaccuracies. As a result, the output of the sensing device 68 may have some offset error and be dependent on temperature. In order to compensate for the above parameters, typically a signal conditioning scheme is utilized. In the example shown in FIG. 5, a Wheatstone bridge configuration is used to measure the resistance variations with two current sources $I_1$ and $I_2$.

As indicated above, $R_{x1}$ and $R_{x2}$ change in opposite direction as a function of strain or equivalently blood pressure in the heart as: $R_{x1}=R_{01}(1+GF \cdot x)$ and $R_{x2}=R_{02}(1+GF \cdot x)$ where $R_{01}$ and $R_{02}$ are the sensor resistances at zero strain, GF is the gauge factor of the sensing device 68, and x is the strain. The two current sources $I_1$ and $I_2$ complete the bridge, and are preferably integrated into the processing module 32 as shown in FIG. 5. In order to cancel out the resistor mismatch, TCR, and TCGF, the following equations should be valid: $R_{01}I_{02} - R_{01}I_{01} = 0$; and $TCI = -(TCR + TCGF)$; where TCI represents the temperature coefficient of the current sources, $R_{01}$ and $R_{02}$ represent the resistor values at the reference temperature, and $I_{01}$ and $I_{02}$ represent the current of the two current sources at the reference temperature. The technology used to implement the processing module 32 should be capable of implementing a current source with any specific temperature coefficient, and the current sources should preferably be designed to have the lowest possible supply voltage sensitivity.

Figure 6:
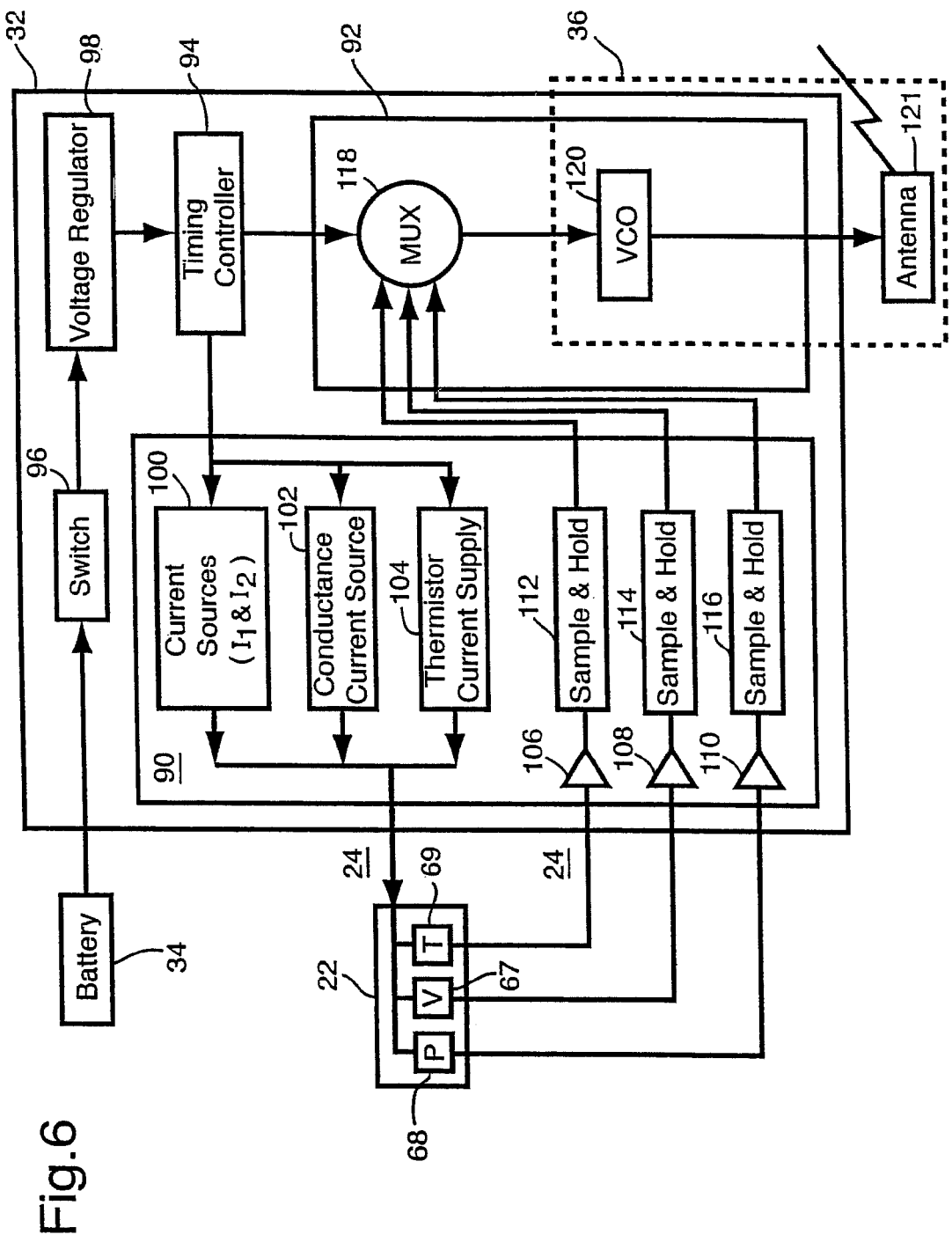
FIG. 6 is a schematic diagram of the transmitter processing module of FIG. 2.

A block diagram of the transmitter processing module 32 is shown in FIG. 6. The module 32 comprises a sensing block 90 and a transmitting block 92 controlled by a timing controller 94. The battery 34 which is connected to the module 32 may be controlled by a switch 96. The battery 34 is preferably a miniature battery of a suitable size and having a battery life that is as long as possible. A suitable battery has a life of 180 mAh, weight of 2.3 g, 1.5 Vdc, and a volume of 0.57 cc. The switch 96 may be, e.g., magnetic or radio controlled, i.e. any suitable device capable of controlling the main power to the module 32 from the battery 34. Between the timing controller 94 and the switch 96 is a voltage regulator that provides a regulated voltage to the timing controller 94 for controlling the blocks 90 and 92. With the above battery specifications, a suitable regulated voltage is a 1V output.

The sensing block 90 includes a current source block 100 for the pressure sensing device 68 (described above with current sources $I_1$ and $I_2$) to compensate for sensor non-idealities, and are the basis of temperature compensation for the pressure sensing device 68. The block 90 also includes a conductance current source 102 for generating the electric field using the electrodes 60 and 62; and a thermistor current supply 104 for the temperature sensing device 69, that preferably comprises a high resistance thermistor for minimal current drain. The outputs from these current sources (100-104) are sent to the sensing tip 22 over the path 24.

The measurements acquired by the sensing devices 67, 68 and 69 are sent back to the sensing block 90 over the path 24. The temperature signal is fed through an amplifier 106 and sampled and held for transmission by a sample and hold component 112. Similarly, the pressure signal is fed to an amplifier 110 and sample and hold component 116; and the volume signal is fed to an amplifier 108 and sample and hold component 114. The amplifiers 106, 108 and 110 are preferably used to encourage the fidelity of the signals. The sample and hold components 112, 114 and 116 hold the signal samples while the timing controller 94 switches power from the sensing block 90 to the transmission block 92.

The transmission block 92 has a multiplexer 118 and a voltage controlled oscillator (VCO) 120. The multiplexer 118 will read the samples from the blocks 112-116 and arrange the signals for transmission by the VCO 120. For example, the multiplexer 118 may arrange the signals in sequential order for transmission. The VCO 120 is connected to an antenna 121 and together make up the transmitter 36 shown in FIG. 2. A suitable VCO 120 is a Colpitts type that consumes an average current of 32 µA. The antenna 121 is preferably connected in parallel with the frequency determining inductor of the VCO 120, and preferably serves as an FM transmitter with a 42 MHz transmission frequency.

Figure 7:
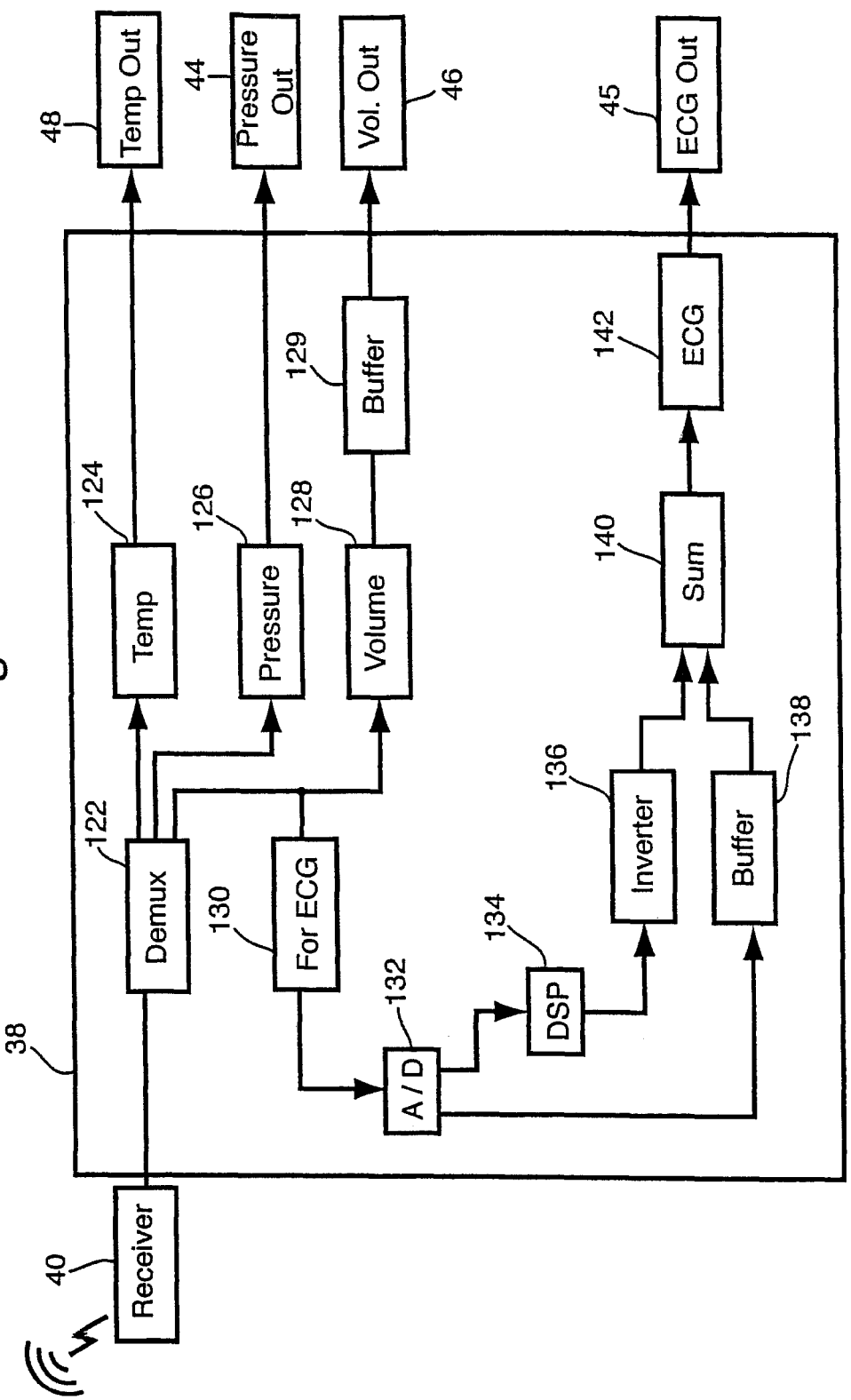
FIG. 7 is a schematic diagram of the receiver processing module of FIG. 2.

A block diagram of the receiver processing module 38 is shown in FIG. 7. The module 38 comprises a demultiplexer 122 connected to the receiver 40 of the receiving device 26. The demultiplexer 122 separates the signals that have been transmitted by the transmitter 36 and received by the receiver 40. If the signals are transmitted as analog signals, the demultiplexer 122 separates the received signal into individual analog signals, and in this example would provide three individual signals, a temperature signal 124, a pressure signal 126, and a volume signal 128. The temperature signal 124 may be immediately available as output 48, and the pressure signal 126 may be immediately available as output 44 for further processing and/or transmission to the computing device 52. It will be appreciated that the module 38 may also comprise a further internal component for processing and analysing the signals 124, 126 and 128, e.g., for display purposes. Moreover, the module 38 may comprise an alarm or other device to notify a wearer of the receiving device 26 of abnormal heart conditions. The display 28 may also be used with such additional processing to output heart parameters or a computed index that represents heart health.

The volume signal 128 may be sent through a buffer 129 and be available as output 46. The volume signal 128 may also be captured at block 130 for further processing to extract the ECG signal. This preliminary signal 130 is preferably converted using an analog-to-digital converter (A/D) 132, which enables signal manipulation while preserving the integrity of the original signal. It will be appreciated that the A/D 132 would not be needed if the signals received have already been converted to digital signals. The A/D 132 has two identical outputs, one of which is input to a digital signal processor (DSP) 134. The DSP 134 is used to clean the ECG signal from the volume signal, and allows for complex signal processing. The extraction of the ECG signal is described in greater detail later.

The signal emerging from the DSP 134 is inverted by an inverter 136. The inverter 136 may also be part of the DSP 134. The other output from the A/D 132 is buffered by the buffer 138 and the inverted signal and the buffered signal are summed at 140 to produce the ECG signal 142 that may also be available as output 45. The buffer 138 is used to maintain the synchronicity of the raw volume signal and the digitally manipulated version (i.e. by the DSP 134). The delay imposed by the DSP 134 would otherwise affect the results of the sum 140. The summer 140 adds the two volume signals, and since one has been inverted, the conductance part of the volume signal will be eliminated and the remaining signal will represent the ECG signal 142.

Figure 8:
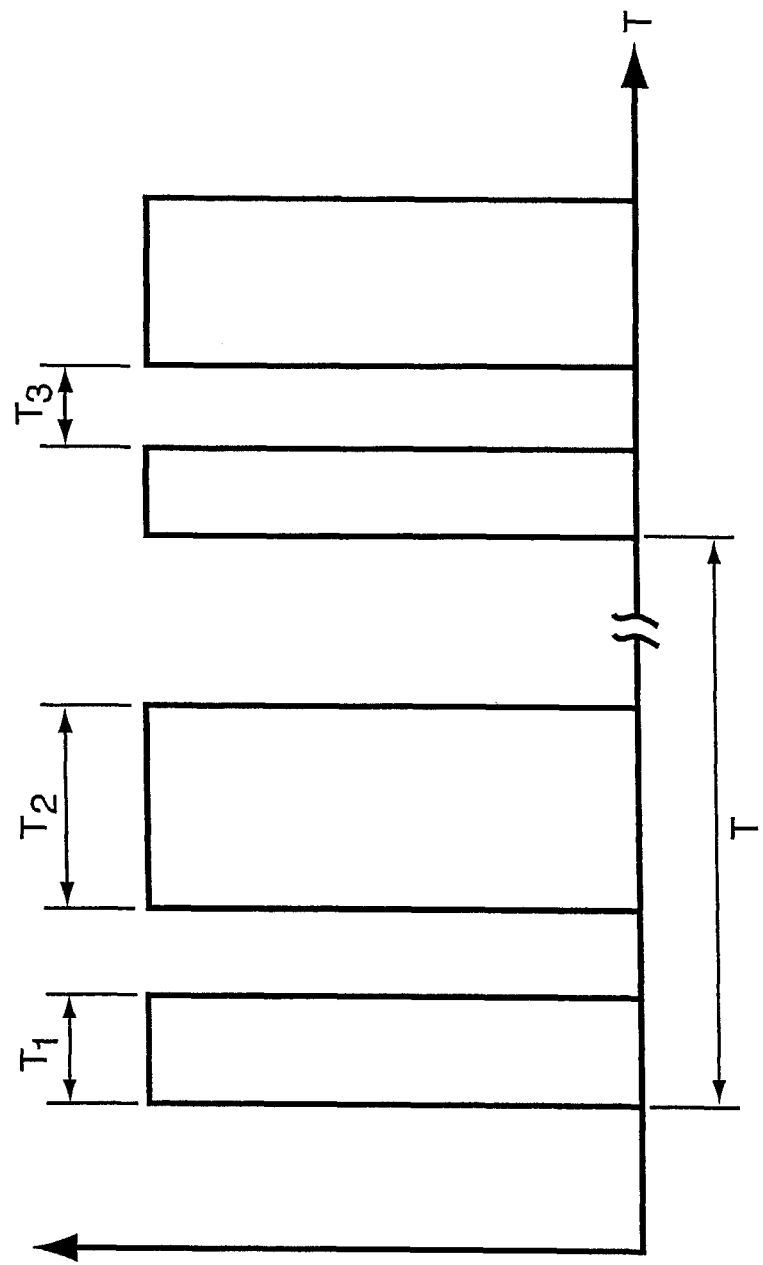
FIG. 8 is a timing diagram for the timing controller of FIG. 6.

The sensing block 90 and the transmitting block 92 are selectively powered using the timing controller 94 in order to conserve power. A timing diagram is shown in FIG. 8 illustrating the operation of the timing controller 94. The period T represents an entire monitoring cycle for the system 10 including measurement and transmission. Specifically, $T_1$ represents the period in which the sensing block 90 is powered in order to obtain the necessary measurements and sample and hold the signals; and $T_2$ represents the period in which the transmitting block 92 is powered in order to execute transmission of data from the transmitting device 20 to the receiving device 26.

For example, a 2 kHz sampling rate provides a period T of 500 µs to sample and transmit data. If the acquisition period $T_2$ is 20 µs, and transmission period $T_3$ is 50 µs, there exists 430 µs during each cycle, in which either the block 90 or the block 92 is waiting. The timing controller 94 uses this timing scheme to selectively turn off either the block 90 or block 92 that is not being used to conserver power, which provides an increase in battery life.

Another benefit arises from using such an energy saving timing scheme, namely the reduction of noise. Specifically, since the block 90 is powered whilst the block 92 is not, the transmitter 36 will not be affected by the noise generated by the signal conditioning, and, conversely, the sensing circuitry (block 90) will not be subject to noise from the transmitter 36. A 10 μs period, represented by $T_3$, is left between the end of one period and the beginning of the next, which enables any circuitry that needs stabilizing to do so.

Therefore, since the transmitting block 92 typically cannot transmit data that has not yet been collected, it would be wasting power while the sensing block 90 is performs its function. If the transmitting block 92 is turned off when it is not needed, power is not consumed, and thus conserved. Similarly, the sensing block 90 typically is not adding any data while the transmitter 36 is sending the previous sample, and thus does not need to consume power during that time.

Figure 9:
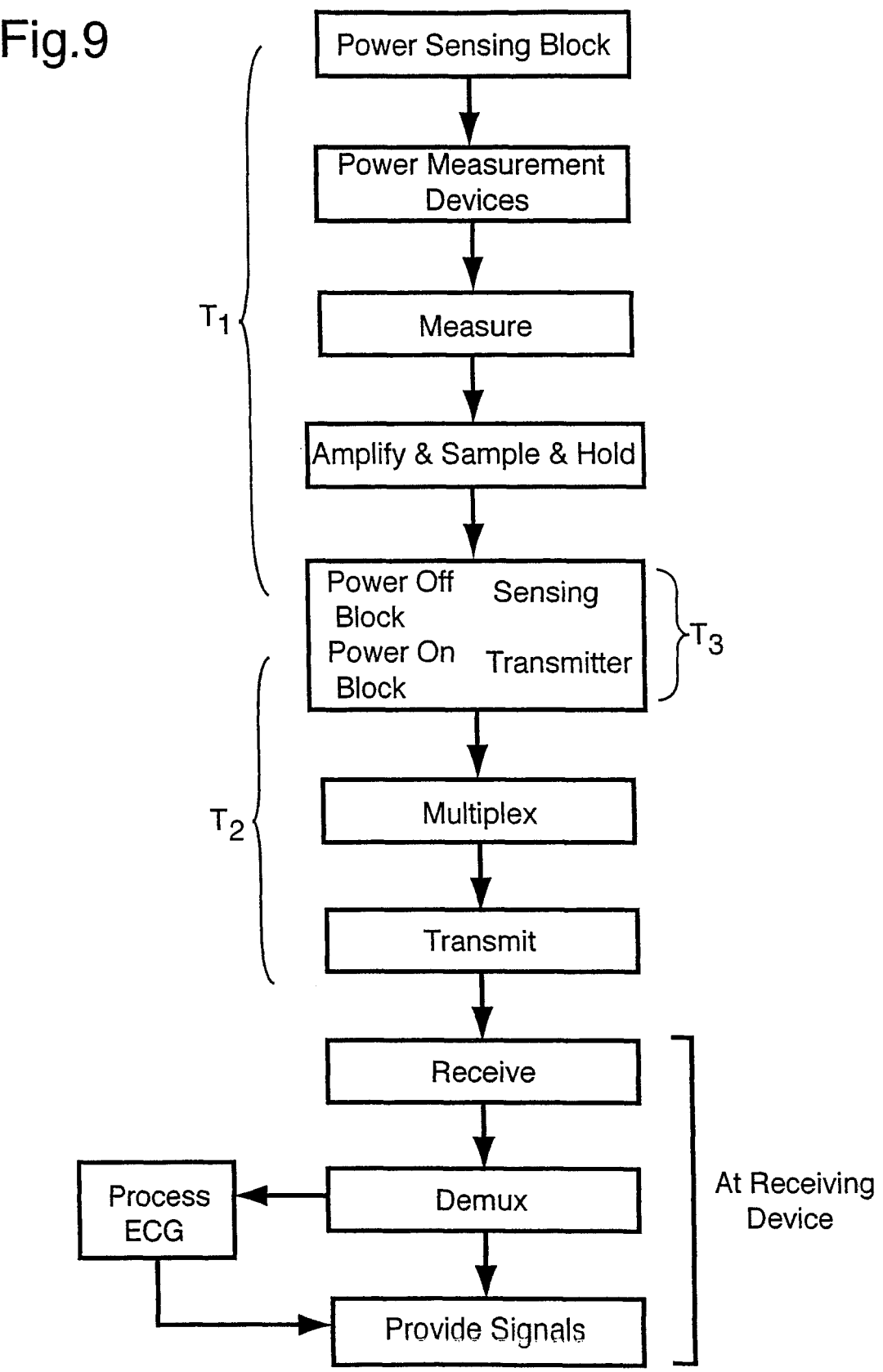
FIG. 9 is a flow chart showing an acquisition and transmission cycle.

FIG. 9 shows a flow chart illustrating an example of the steps taken by the system 10 during one complete cycle T, and the subsequent processing by the receiving device 26. The sensing block 90 is powered which enables the current sources to power the measurement devices 67, 68 and 69 and obtain the measurements. These measurements are then amplified and undergo a sample and hold. The sensing block 90 is then powered "off" and the transmitting block 92 is powered "on", wherein the time lag between theses steps is represented by $T_3$ as explained above. Once the block 92 has power, the multiplexer 118 is then able to obtain the signals stored in the sample and hold components 112-116, and combine these signals for transmission. In this example the multiplexer 118 preferably operates by arranging the signals in a particular sequential order that would be known to the demultiplexer 122 in order to enable the demultiplexer 122 to separate the signals at the receiving end.

The multiplexer 118 passes this "combined" signal to the VCO 120 that uses the antenna 121 to transmit the "combined" signal to receiving device 26. At this point, a complete measurement cycle has been executed, and the signal that has been transmitted continues to the receiving device 26 for further processing and/or output. The transmitting device 20 may then repeat this cycle as required or desired.

The receiving device 26 receives the "combined" signal from the receiver 40. The signal is passed to the demultiplexer 122 where it is separated into its components. The temperature and pressure signals 124 and 126 respectively, may be available as outputs or for further processing by the module 38. The volume signal 128 may be buffered and output at 46, and may also be obtained for extracting the ECG signal 142 and providing output 45. The extraction of the ECG signal 142 from the raw volume signal 128 is described in greater detail below, while referring to the functional blocks shown in FIG. 7 that relate thereto.

As indicated above, the conductance or volume signal 128 acquired using the volume sensing device 67 is used to extract the ECG signal 142.

The conductance signal acquired using the volume electrodes 67 consists of the conductance value of the blood in the LV 16, any noise generated by the system or in the environment, and the ECG signal 142 that is picked up as a component of environmental noise. As described above, in this example, the raw signals are collected and transmitted, e.g., as a combined analog waveform, without performing any signal conditioning, to the receiving device 26. When the combined signal is received by the receiving device 26, the individual pressure, volume and temperature signals (124, 126 and 128) are separated, and a process begins to separate the various components of the volume signal 128 (i.e. at 130).

The conductance signal 128 is the result of an electrical field generated, by means of the electrodes 60, 62, from the apex of the heart to the carotid artery. Due to myocardial contact of the conductance rings, the resulting conductance signal will also carry the ECG signal. It is generally common practice to use signal conditioning and filtering to eliminate the environmental and ECG noise components to extract the conductance signal 128. In this embodiment, signal conditioning is used to not only remove the ECG component of noise to extract the conductance signal, but also to separately condition the ECG signal 142 to remove the conductance portion of the signal. The result is that an ECG signal 142 can be collected without introducing any additional instrumentation into the LV 16. Therefore, the sensing tip 22 can be used to provide a more thorough cardiac assessment, using a single device.

Once the signal is obtained at 130, an A/D converter 132 in the processing module 38 converts the raw signal to a digital signal and passes the signal to each of an ECG digital signal processor (DSP) and a buffer 138. Once the respective signals are processed, they are summed and a final ECG signal 142 is produced.

Figure 10:
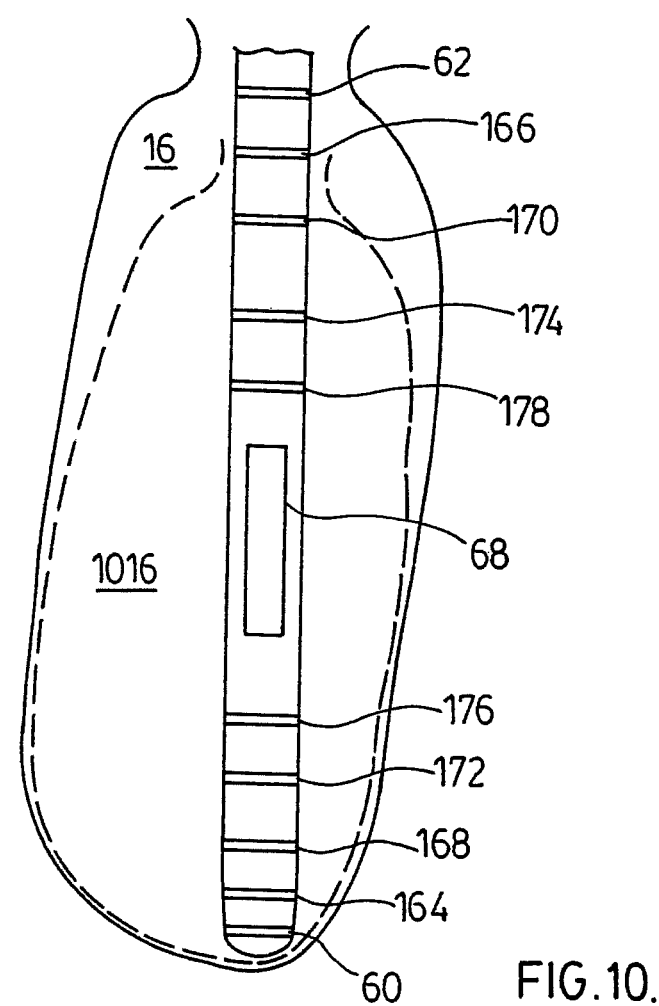
FIG. 10 shows another embodiment of the sensing tip of FIG. 3.

In another embodiment, the volume sensing device 67 comprises a plurality of inner electrode rings, for example four as shown in FIG. 10. Since the optimal conductance measurement is performed by transmitting along the entire length of the LV 16, and different organisms have different sized hearts 12, it may be desirable to incorporate multiple sets of inner electrode ring pairs. In FIG. 10, the LV 16 shown in FIG. 3 is provided, as well as an LV 1016 from a smaller organism shown in dashed lines. The pair 164, 166 is similar to the pair 64, 66 described above, however, the sensing tip 22 now includes the pairs 168, 170; 172, 174; and 176, 178 arranged progressively closer together and situated between the outer electrode pair 60, 62.

In such an embodiment, it may be possible to selectively operate any of the electrode rings as a transmitting ring, but typically the electrode 60 would remain as the receiving electrode. In the example shown in FIG. 10, the electrode 170 would be selected as the optimal transmitting electrode for the LV 1016 and then the inner sensing electrode pair would comprise the electrodes 164 and 174. Therefore, numerous configurations of receiving, and sensing electrodes can be selectively chosen in order to obtain an optimal conductance signal, depending on the size of the LV (e.g. 16 or 1016).

Therefore, the system 10 enables the monitoring of a heart in a living organism by measuring both pressure and volume in a chamber of the heart, preferably the LV 16. The pressure and volume measurements are acquired using a single sensing tip 22 and are communicated to a transmitting device 20 to be wirelessly transmitted to a receiving device 26, wherein they are used to monitor the heart. The system 10 may also incorporate a temperature measurement that can be transmitted with the volume and pressure measurement to provide further data for monitoring. The system 10 may also extract an ECG signal from the volume measurement. This allows the monitoring of up to four signals that can be used to determine the health of a heart.

In addition to a compact design, the system 10 may also incorporate an energy saving timing scheme that reduces the power required per acquisition cycle and thus increases the operational lifetime of the transmitting device 20.

As noted above, a calibration scheme and resistivity meter can also be incorporated into a system such as system 10. In yet another embodiment, shown in FIG. 11, catheter 22 includes a resistivity sensor (generally numeral 200). In one implementation, resistivity sensor 200a comprises a series electrodes 202 arranged substantially parallel to the axis of the catheter 22. In another implementation, resistivity meter 200b comprises a set of spaced apart rings 204, e.g. four. The spacing is such that D is less than the diameter of the rings 204. The resulting field is thus small enough that it does not experience any significant effect from changing volume. In general, the resistivity sensor 200 can be configured using any four electrodes spaced such that the distance apart of the further electrodes does not exceed the diameter of the catheter.

The resistivity sensor 200 operates on a similar principle to that of a conductance catheter. Four electrodes are deployed in series, and a constant current flows through the fluid. The current travels between the two outermost electrodes 204. The two inner electrodes are used to sense the voltage created by the resistance of the blood. By measuring voltage and by applying a known current, the resistance can be obtained according to the relationship V=IR.

Figure 11:
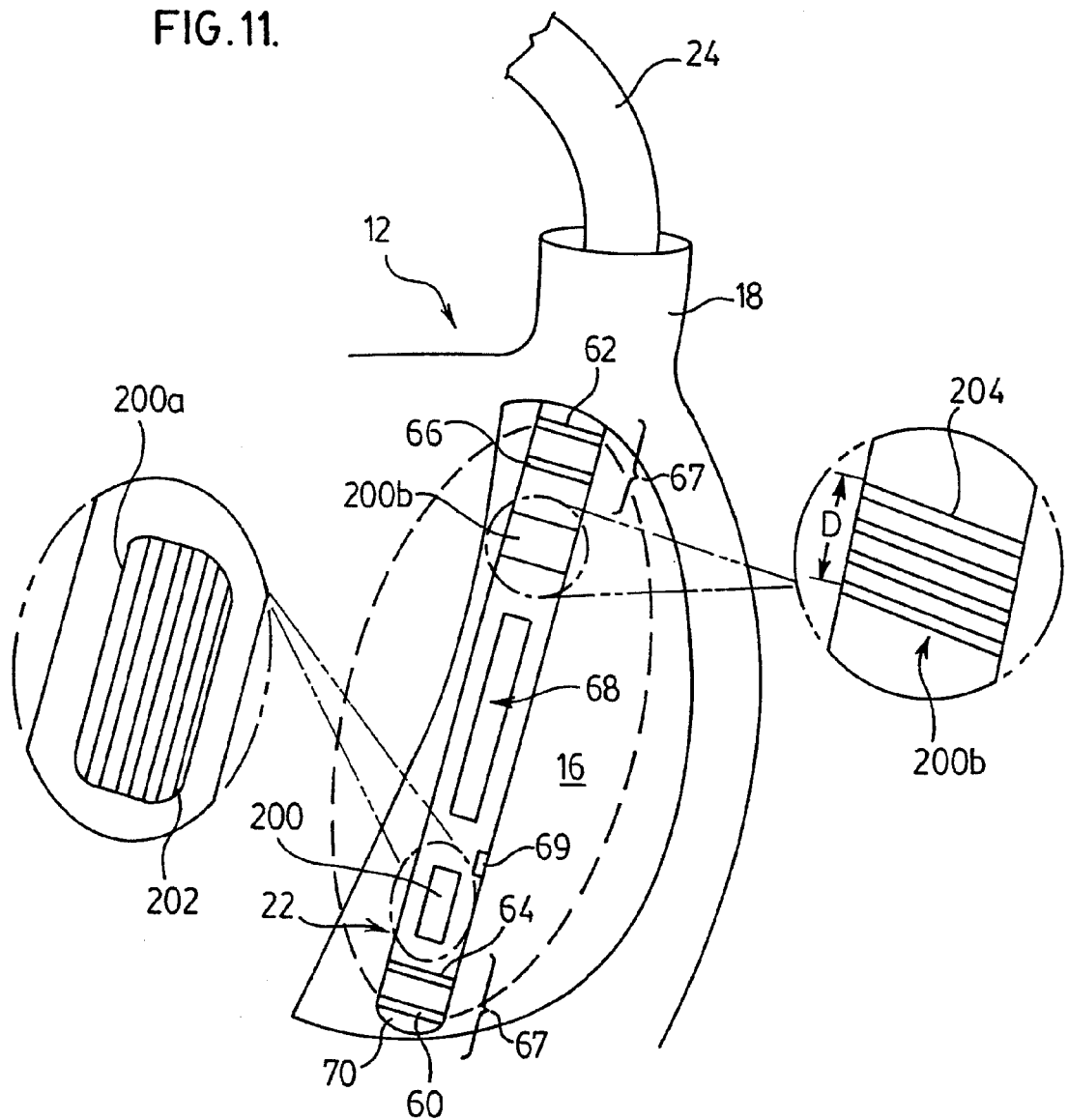
FIG. 11 shows a sensing tip having a resistivity sensor.

Using the configuration shown in FIG. 11, a continuous or as-needed resistivity measurement can be made, which in turn enables more accurate blood volume measurements.

As noted above, the resistivity sensor 200 can be used to measure the volume of any fluid, e.g. by considering the equation for a volume of fluid in a cylinder, namely $V=\rho L^2 G$. This equation is a simplified version of the typical equation used to measure LV volume, namely where $\alpha=1$ and disregarding any correction factor for G. It has been found that if $\rho$ changes in a cylindrical volume, the volume reading changes by a directly proportional amount, even though the volume in the cylinder is actually the same. By using the resistivity sensor 200, the value for $\rho$ can be changed at any time and to any desired degree, while not changing the value for the volume of the fluid. This enables the system to be calibrated using a known volume, independent of the value for $\rho$.

It can therefore be seen that by incorporating a resistivity sensor 200, an accurate and current resistivity value can be obtained in real time rather than relying on the accuracy of the latest measurement. Also, where resistivity measurements are obtained by drawing blood, significant discomfort can be avoided. Although two different variations of sensor 200 are shown, it will be appreciated that typically only one variation would be used.

Figure 12:
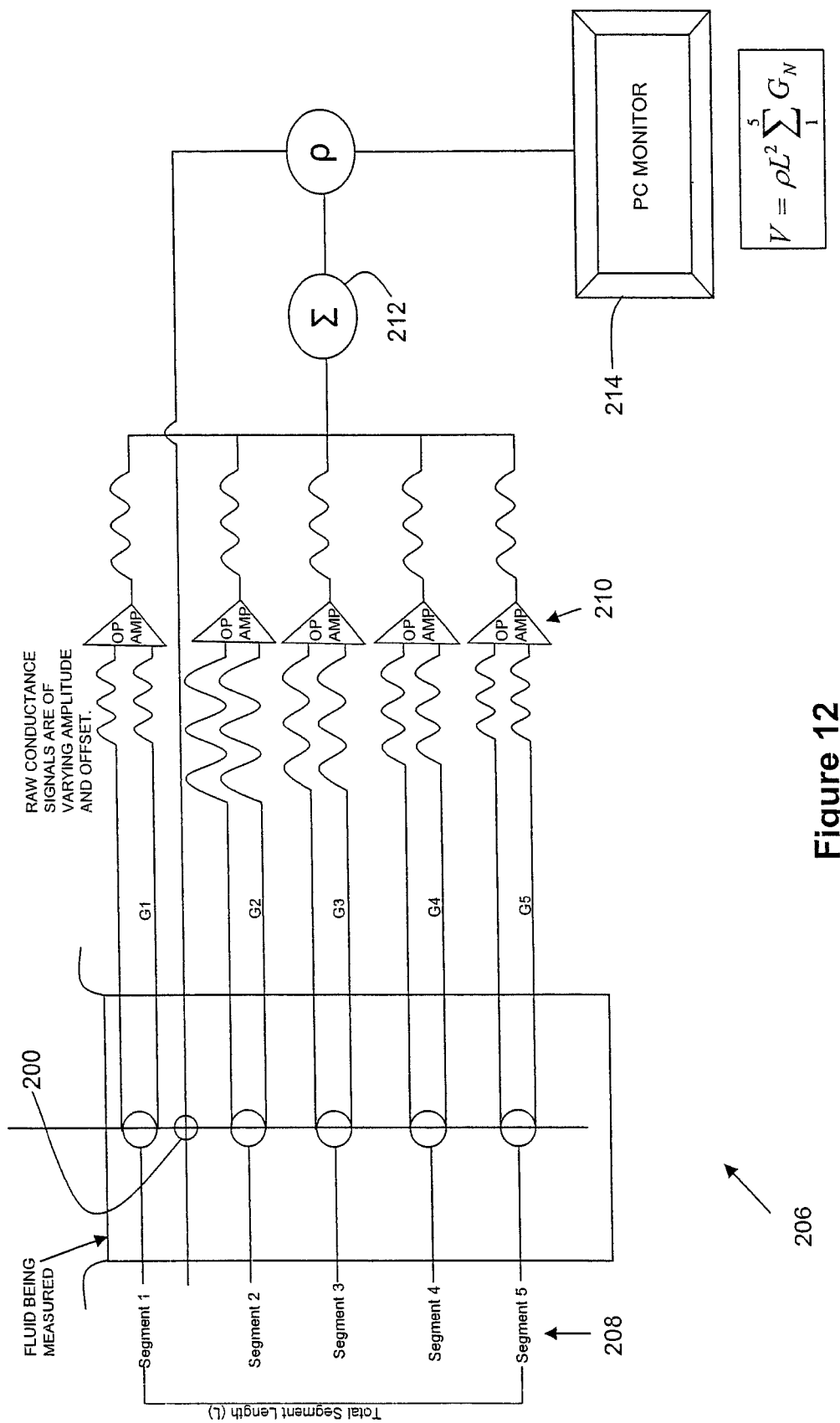
FIG. 12 shows a circuit for measuring fluid volume.

A schematic diagram of a volume measurement circuit 206 is shown in FIG. 12. The circuit 206 provides a comprehensive system for calibrating conductance signals for estimating blood volume, e.g. in an LV. The electric field distribution from a dipole catheter is a series of concentric rings emanating from the distal and proximal rings, as discussed above. Due to this configuration, the voltage sensed by different ring segments 208 varies depending on where they are located in the field. The effect is similar to a line of listeners in front of a speaker: those is the front will hear a louder signal than those in the rear.

In the circuit 206 shown in FIG. 12, each segment 208 of the catheter 22 is assigned an individual gain and offset circuit 210. This enables a custom gain to be applied to each pair of rings. The effect of adjusting the gain is beneficial for both signals that may be too "weak" as well as those that could be too "strong". In either case, interpretation can be affected and thus compensating for such effects improves the quality of the measurement. As can be seen in FIG. 12, the segments are summed at stage 212 and a display 214, e.g. a PC monitor is used to view the volume measurement.

In order to set the individual gains, a calibration fluid having a known conductance value can be used, which corresponds to the fluid being measured, (blood or otherwise). This allows the signals to be normalized In general, the catheter 22 is placed in a well containing a fluid of a known conductance value. The readings can then be displayed on an electronic display. The circuit then adjusts the gains for the individual segments such that the signals are all reading the same voltage output for a given solution. In addition to adjusting voltage amplitude, the circuit 206 can also adjust for baseline voltage such that all the signals have the same span and output for a given segmental volume. The calibration fluid can also be used to calibrate the system 10 for linear output of volume. By using a series of graduate volumes, the output of the catheter 22 can be recorded as it moves from one volume to the next.

The calibration system can also use a series of wells into which is placed fluids of differing but know conductivities. This enables verification of the linearity of the system 10 as it measures the value of conductance G for each solution. The voltage outputs can be displayed in a plot to verify linearity and hence accuracy of the system.

Figure 13:
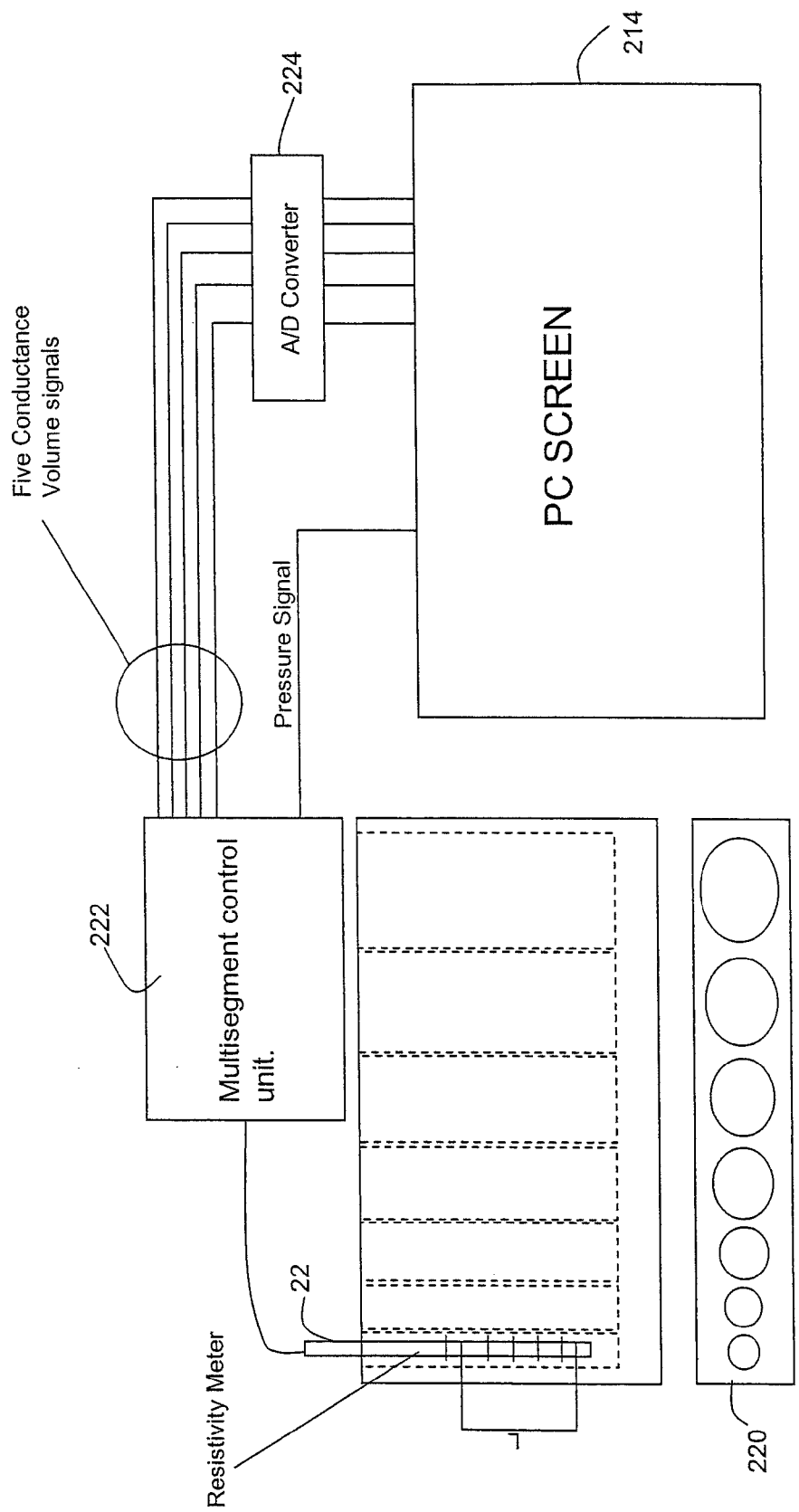
FIG. 13 shows a calibration circuit.
Figure 14:
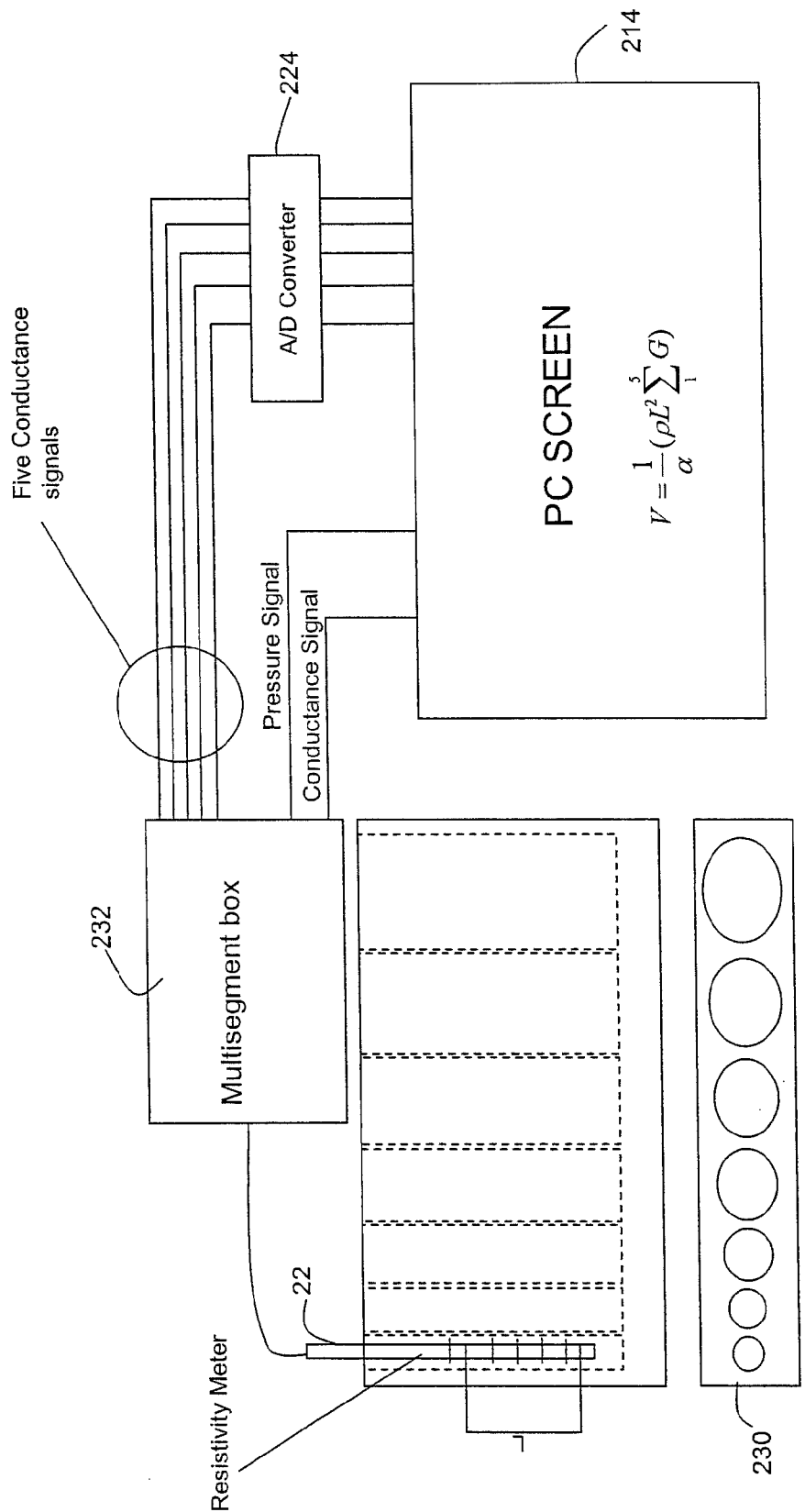
FIG. 14 shows another calibration circuit.

FIGS. 13 and 14 illustrate two arrangements for calibrating the catheter 22 to account for the actual and varying sensitivity of the electrodes (60-66).

In the arrangement shown in FIG. 13, two wells of known volume in a volume cuvette 220 are used to determine the volume calibration slope. In the example shown in FIG. 13, a multi-segment control box 222 connected to the catheter 22 provides a segmental output that is proportional to the volume of liquid defined by the diameter of the cylinder in the cuvette 220, and the spacing of each of the segments 208. As noted above, the $\rho$ sensor 200 incorporated into the catheter 22 can be used to compensate for any change in $\rho$ that may occur. By determining the value of $\rho$ and incorporating such a value into the calibration measurement, it is possible to change the $\rho$ value of the fluid being measured, without changing the output voltage. The volume measured is then independent of $\rho$. For this arrangement, the actual value of conductivity is not required. It can be seen that in this arrangement, a correction factor can be maintained if it should change.

The control box 222 also includes the gain and offset circuitry 210, which is adjusted such that all the segments 208 deliver the same voltage when in a given cuvette well. The gain/offset circuit 210 can be applied in the same way regardless of the method of calibration. For example, using 20 and 50 ml volume wells, when placed in the 20 ml volume well, the following readings may be observed, shown in Table 1 below:

TABLE 1

Example calibration readings

| Segment | V@20 ml | V@50 ml | Gain/Offset correction @20 ml | Gain/Offset correction @50 ml |
|---|---|---|---|---|
| 1 | 2 | 6 | −2 | 0 |
| 2 | 0 | 3 | −2 | 0 |
| 3 | 5 | 8 | −2 | 0 |
| 4 | 3 | 5 | −2 | 0 |
| 5 | −1 | −2 | −2 | 0 |

One concern is that with a +/−10 volt A/D 224, the range could be exceeded if the properties of the fluid change, e.g. when a saline bolus in injected to correct for parallel conductance caused by myocardial contribution. The system described herein enables the user to dial in the span and gain desired by the user and being suitable to a wide range of subjects. The $\rho$ sensor 200 in this arrangement would not need to be calibrated as it would not see a volume change going from one cuvette well to another. The sensitivity of the $\rho$ sensor 200 can be corrected however if it is not reading the correct values for the fluid. This can be done since in the arrangement shown, the $\rho$ values are known for each fluid.

Being able to account for varying electrode sensitivities can be beneficial for the accuracy of the measurements.

The output from the control box 222 is fed into an A/D converter 224 and the volume is calibrated according to the linear relationship y=mx+b. Two of the cuvette wells, with known volumes, can thus be used to determine the value for m. In this arrangement, the value of ρ is being compensated for in the control box 222. It is also possible to output the value of ρ to the PC 214 and use it as a scaling factor for the volume calibration.

In the arrangement shown in FIG. 14, an equal volume cuvette 230 can be used, which has a plurality of wells with equal volumes. To calibrate, a fluid having a known and precise value of conductance can be inserted into each well. In this arrangement, a control box 232 provides a segmental output that is proportional to the conductance of the liquid defined by the diameter of the cylinder (fluid well) and the spacing of each segment 208. Both the conductance and resistivity voltages generated by the calibration fluids are sent from the control box to the PC 214, with the segmental output again being fed through A/D converter 224. The PC 214 determines the slope for both the conductance G and the resistivity ρ and the values for each segment are summed to provide $G_{total}$.

The values of ρ and G are applied to the volume formula $$V = \frac{1}{\alpha}\rho L^2 G.$$

Since both ρ and G have been obtained in a controlled and accurate method and can be monitored on an ongoing basis, the total volume accuracy can be maintained.

It will be appreciated that the calibration of the circuit 206 can be done prior to use of the catheter 22, but may also be configured to be performed periodically while the catheter 22 is deployed to enable real time calibration. In this way, a known voltage can be used to represent a conductance level.

It has also been found that the position of a catheter or other measuring device can be determined by comparing the excitation and measured conductance waveforms using a phase angle detector. By comparing such waveforms, it is possible to observe a phase shift between the two waveforms, which is caused by the capacitive nature of the myocardium. This is caused by the catheter being off-centred in the ventricle. An AC waveform moving through a capacitor will incur a phase delay. Since blood is a purely resistive material, it does not add appreciably to the observed phase shift. As will be discussed below, it has been recognized that by superimposing the sinusoidal electrode stimulation waveform with the sinusoidal sensed voltage waveform, the catheter electrode position within the ventricle can be determined.

The above can be incorporated into a real-time feedback scheme that allows the use of such a measurement of phase-angle to adjust the catheter electrode position so that they are in the optimum position within the ventricle. Optimum positioning is obtained when the phase angle is at a minimum, indicating that the electric field is in a center position that minimizes field incursion into the myocardium.

Figure 16:
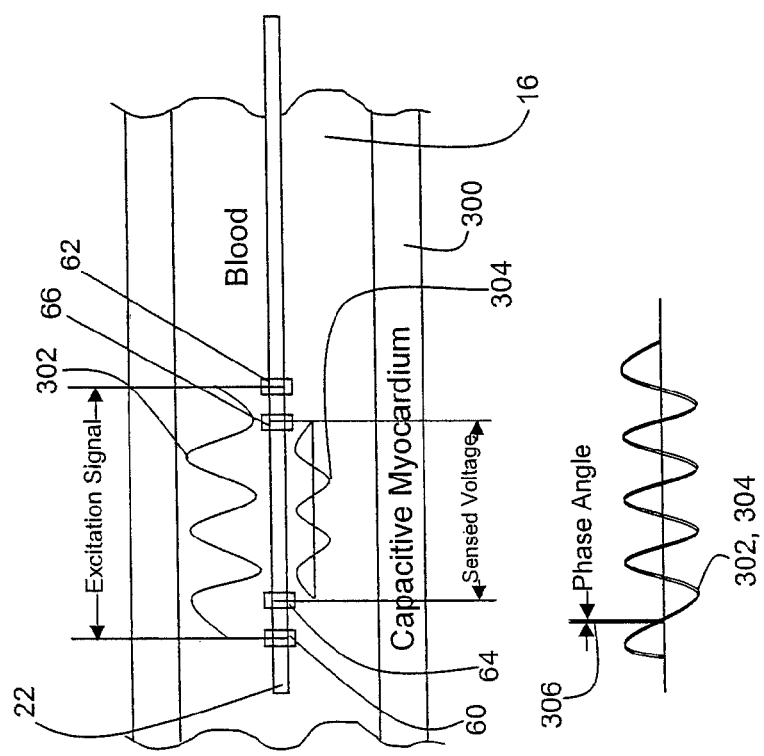
FIG. 16 illustrates a sectional view of a centred catheter in the ventricle of FIG. 15.
Figure 15:
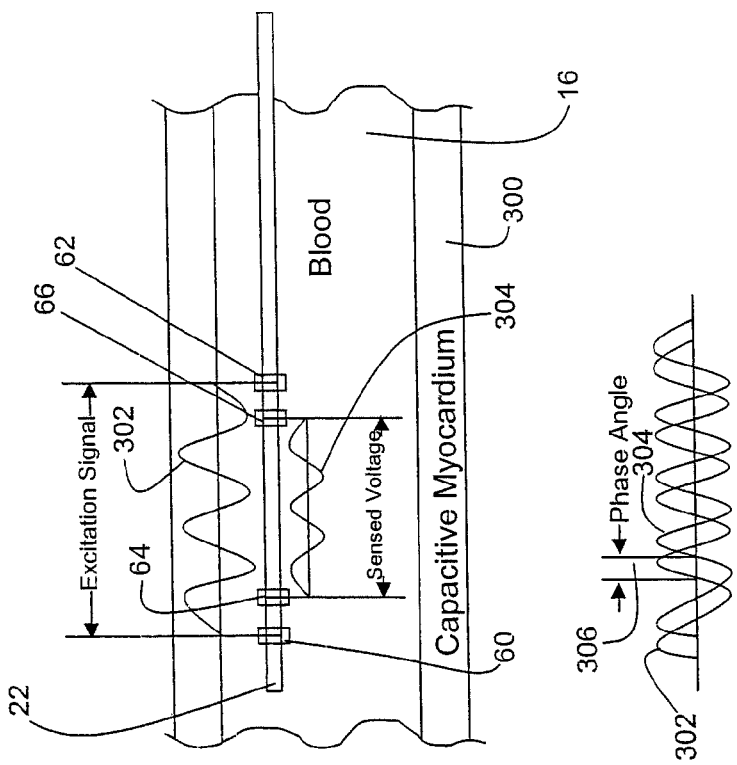
FIG. 15 illustrates a sectional view of an off-centred catheter in a ventricle.

Turning now to FIGS. 15 and 16, a sectional view of a ventricle 16 is shown. In FIG. 15, the sensing tip 22 of a catheter is offset or off-centred in the ventricle 16 and thus it can be seen that the excitation signal 202 is affected by the capacitive effect of the myocardium 300. The sensed voltage 304 is thus offset from the excitation signal 302 thus creating a phase angle 306 when the two waveforms are observed. It will be appreciated that the waveforms 302, 304 can be viewed using any monitoring equipment, e.g. in real-time measurements, during calibration stages etc. FIG. 16 shows that by centering the sensing tip 22 in the ventricle 16, the excitation signal 302 travel substantially through the blood rather than the capacitive myocardium 300 and thus the phase angle 306 is minimized. Based on this observation, the waveforms 302, 304 can be superimposed in a display as shown in FIGS. 15 and 16 (e.g. using display 214 or terminal 52) to provide feedback to a user so that the positioning of the sensing tip 22 can be adjusted until the phase angle 306 is minimized thus indicating when the sensing tip 22 is substantially centered. In another embodiment, the zero-crossings of the waveforms can be compared to provide a numerical offset factor that can be observed as the sensing tip 22 is adjusted until this offset value is minimized By providing such feedback, further accuracy of the volume measurement can be attained.

Although the invention has been described with reference to certain specific embodiments, various modifications thereof will be apparent to those skilled in the art.

The invention claimed is:

1. A method for positioning a sensing tip disposed in a ventricle, the method comprising:
    obtaining an excitation waveform generated by one pair of electrodes disposed on said sensing tip;
    obtaining a conductance waveform sensed by another pair of electrodes disposed on said sensing tip;
    enabling said waveforms to be compared to determine a phase shift between said waveforms; and
    identifying when said phase shift is deemed acceptable due to adjustment of said positioning.

2. The method according to claim 1 wherein said enabling comprises superimposing said waveforms to provide a visual indication of said phase shift.

3. The method according to claim 1 further comprising determining said phase shift by comparing zero-crossings of said waveforms.

4. The method according to claim 1 performed in real time while said sensing tip is measuring volume of fluid in said ventricle.

5. The method according to claim 1 performed during a calibration operation.

6. A non-transitory computer readable medium for facilitating positioning a sensing tip disposed in a ventricle, the computer readable medium comprising computer executable instructions for:
    obtaining an excitation waveform generated by one pair of electrodes disposed on said sensing tip;
    obtaining a conductance waveform sensed by another pair of electrodes disposed on said sensing tip;
    enabling said waveforms to be compared to determine a phase shift between said waveforms; and
    identifying when said phase shift is deemed acceptable due to adjustment of said positioning.

7. The computer readable medium according to claim 6 wherein said enabling comprises superimposing said waveforms to provide a visual indication of said phase shift.

8. The computer readable medium according to claim 6, further comprising computer executable instructions for determining said phase shift by comparing zero-crossings of said waveforms.

9. The computer readable medium according to claim 6 further comprising computer executable instructions for performing said obtaining said excitation waveform, said obtaining said conductance waveform, said enabling and said identifying, in real time while said sensing tip is measuring volume of fluid in said ventricle.

10. The computer readable medium according to claim 6 further comprising computer executable instructions for performing said obtaining said excitation waveform, said obtaining said conductance waveform, said enabling and said identifying, during a calibration operation.

\* \* \* \* \*